United States Patent
Mecke et al.

(10) Patent No.: US 10,209,204 B2
(45) Date of Patent: Feb. 19, 2019

(54) X-RAY INSPECTION SYSTEM AND METHOD FOR ROTATING A TEST OBJECT BY MEANS OF SUCH AN X-RAY INSPECTION SYSTEM

(71) Applicant: YXLON International GmbH, Hamburg (DE)

(72) Inventors: Andreas Mecke, Barsbuettel (DE); Jan Spalding, Rellingen (DE); Axel Klein, Hamburg (DE)

(73) Assignee: YXLON INTERNATIONAL GMBH, Hamburg (DE)

( * ) Notice: Subject to any disclaimer, the term of this patent is extended or adjusted under 35 U.S.C. 154(b) by 101 days.

(21) Appl. No.: 15/030,600

(22) PCT Filed: Oct. 21, 2014

(86) PCT No.: PCT/EP2014/002841
§ 371 (c)(1),
(2) Date: Apr. 20, 2016

(87) PCT Pub. No.: WO2015/058855
PCT Pub. Date: Apr. 30, 2015

(65) Prior Publication Data
US 2016/0238541 A1    Aug. 18, 2016

(30) Foreign Application Priority Data
Oct. 21, 2013   (DE) .................. 10 2013 017 462

(51) Int. Cl.
*G01N 23/00*    (2006.01)
*G01N 23/046*    (2018.01)
*G01N 23/04*    (2018.01)

(52) U.S. Cl.
CPC ........... *G01N 23/046* (2013.01); *G01N 23/04* (2013.01); *G01N 2223/309* (2013.01);
(Continued)

(58) Field of Classification Search
CPC .............. G01N 2223/3306; G01N 2223/3308
See application file for complete search history.

(56) References Cited

U.S. PATENT DOCUMENTS

| | | | | |
|---|---|---|---|---|
| 4,809,308 | A | * | 2/1989 | Adams ................. G01N 23/18 378/58 |
| 2004/0096029 | A1 | | 5/2004 | Shiota et al. |
| 2011/0215259 | A1 | | 9/2011 | Iwata |

FOREIGN PATENT DOCUMENTS

| | | |
|---|---|---|
| AT | 363262 B | 7/1981 |
| CN | 1499193 A | 5/2004 |

(Continued)

OTHER PUBLICATIONS

David Haas: "Röntgenbildgebung und Analyse", 2008, XP055160149, Retrieved from the Internet: http://www.alexanderrack.eu/papers/haas2008.pdf, pp. 8-9.

(Continued)

*Primary Examiner* — Dani Fox
(74) *Attorney, Agent, or Firm* — Leydig, Voit & Mayer, Ltd.

(57) ABSTRACT

An X-ray inspection system includes an X-ray source and a detector. A rotary table is arranged between the X-ray source and the detector. The rotary table is configured to secure a test object on the rotary table. The rotary table is arranged on a positioning table. The positioning table is configured to move parallel to an xy-plane between the X-ray source and the detector. The xy-plane is perpendicular to a surface of the detector extending parallel to the xz-plane and the rotary table is configured to rotate about a z-axis.

10 Claims, 5 Drawing Sheets

(52) U.S. Cl.
CPC .......... *G01N 2223/3303* (2013.01); *G01N 2223/3306* (2013.01); *G01N 2223/3308* (2013.01); *G01N 2223/419* (2013.01)

(56) References Cited

FOREIGN PATENT DOCUMENTS

| | | |
|---|---|---|
| CN | 101963587 A | 2/2011 |
| CN | 102188778 A | 9/2011 |
| CN | 102283661 A | 12/2011 |
| GB | 2274964 A | 8/1994 |
| JP | 2003156455 A | 5/2003 |
| JP | 2009174972 A | 8/2009 |
| JP | 2013137287 A | 7/2013 |
| WO | WO 2009078415 A | 6/2009 |

OTHER PUBLICATIONS

International Search Report of PCT/EP2014/002841, dated Jan. 7, 2015, pp. 1-2.

\* cited by examiner

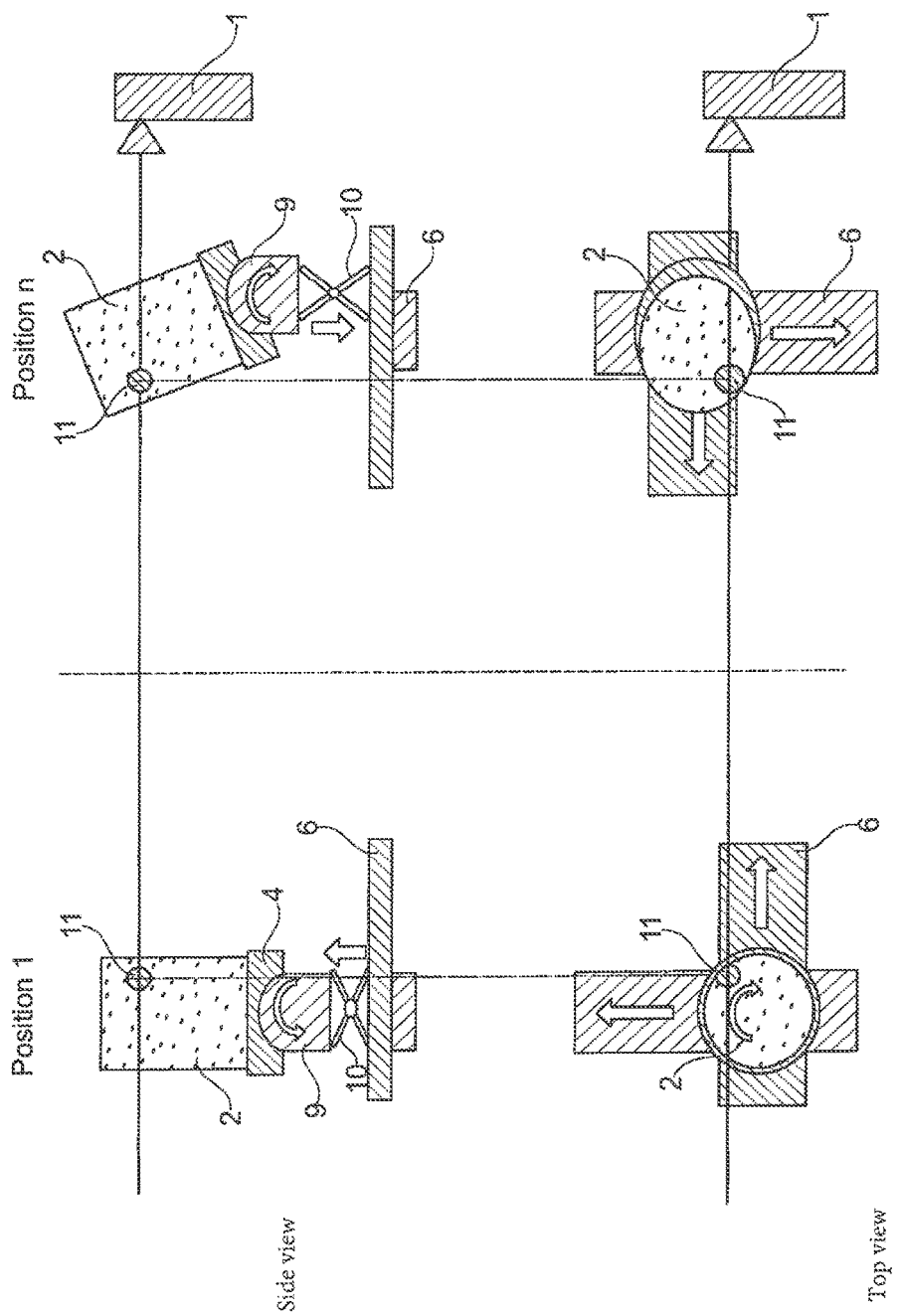

X-RAY INSPECTION SYSTEM AND METHOD FOR ROTATING A TEST OBJECT BY MEANS OF SUCH AN X-RAY INSPECTION SYSTEM

CROSS-REFERENCE TO RELATED APPLICATIONS

This application is a U.S. National Phase Application under 35 U.S.C. § 371 of International Application No. PCT/EP2014/002841, filed on Oct. 21, 2014, and claims benefit to German Patent Application No. DE 10 2013 017 462.7, filed on Oct. 21, 2013. The International Application was published in German on Apr. 30, 2015 as WO 2015/058855 under PCT Article 21(2).

FIELD

The invention relates to an X-ray inspection system with an X-ray source, a detector and a rotary table arranged between them, on which a test object can be secured, and to a method for rotating a test object in such an X-ray inspection system.

BACKGROUND

It is known that in X-ray inspection systems the test object is moved by means of real (physical) axes between the imaging elements X-ray source and detector. It is also quite usual to move both the X-ray source and the detector in order to obtain the desired picture section. In the known solution approaches, if the area of a test object to be examined is to be observed with a particular irradiation angle, it is problematic if this area is not, however, situated in the centre or at least in the required area of the necessary tilting axis or axis of rotation.

For this, there are two solution approaches:
respanning the test object, i.e. the area of interest is moved manually into the centre of the axis of rotation;
adding further axes in order to enlarge the degree of freedom in the corresponding directions.

However, these procedures have decisive disadvantages, such as, for example, increased time consumption, increased axis complexity and reduction of the test volume with an installation space that remains constant.

The above-named manipulation and concomitant problem of angle-dependent manipulation relates to all X-ray systems, both DXR (digital X-ray) and CT (computed tomography) as well as laminography. The problem becomes more acute as the resolution requirement increases. Thus, for example, in the case of a very high-resolution CT system, additional xy-positioning tables are used on the decisive axis of rotation in order to bring the test object into the centre of the axis of rotation which determines the CT quality.

SUMMARY

In an embodiment, an aspect of the present invention is therefore to present an X-ray inspection system as well as a method which require a maximum degree of freedom with little installation space and above all less user interaction.

This aspect is achieved by devices according to the claims. With the X-ray inspection system according to the invention it is possible to carry out one of the rotation methods according to the invention, described in more detail below. The parts mentioned in the claims and the possibilities of movement make it possible to carry out this method according to the invention simply.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following:

FIG. 5 is a schematic representation of a method about a fixable point.

DETAILED DESCRIPTION

An advantageous development of the invention provides that the rotary table can be moved along the z-axis. It is thereby also possible to carry out an examination of the test object that is variable in height.

A further advantageous development of the invention provides that the rotary table can be tilted about a tilting axis running parallel to the xy-plane, in particular parallel to the x-axis. It is thereby possible to select the most favourable possible trajectory of the X-radiation through the test object.

A further advantageous development of the invention provides that the X-ray source, in conjunction with the detector, can be rotated about the rotary table and/or can be moved with respect to the rotary table parallel to the xy-plane and/or can be moved parallel to the z-axis and/or can be tilted about a tilting axis running parallel to the xy-plane, in particular parallel to the x-axis. It is thereby possible, alternatively or additionally to the movement of the test object, to also move the imaging system, with the result that the flexibility of the examination is increased.

An aspect of the invention is also achieved by a method wherein the rotary table is secured on an xy-positioning table, wherein it is possible to proceed with the x-axis and the y-axis combined, with the result that the rotary table moves on an orbit. In order to realize a virtual axis of rotation, it is necessary for the rotation angle of the rotary table to be positioned or moved in the defined relationship to the x- and y-axes. For this, the axis of rotation is defined as master and the two axes x and y are positioned corresponding to the angle of rotation of the axis of rotation, as indicated in the two relationships.

An aspect of the invention is likewise achieved by a method wherein instead of moving the test object, the imaging elements X-ray source and detector are moved. The relationships correspond to those in the case of the combined movement of the test object by means of rotary table and positioning table.

An advantageous development of the invention provides that, before carrying out the described movements, the rotary table is moved in the z direction and is tilted about a tilting axis running parallel to the x direction, with the result that an area of interest lying within the test object lies at the same position in the coordinate system before and after the described tilting movement and translational movement.

This makes it possible, in the case of a test object, to carry out the examination of the test object at any desired point within the test object about an axis aligned as desired. The user can thus decide individually which parameters are desired and achieve the best possible result.

Figure 1:
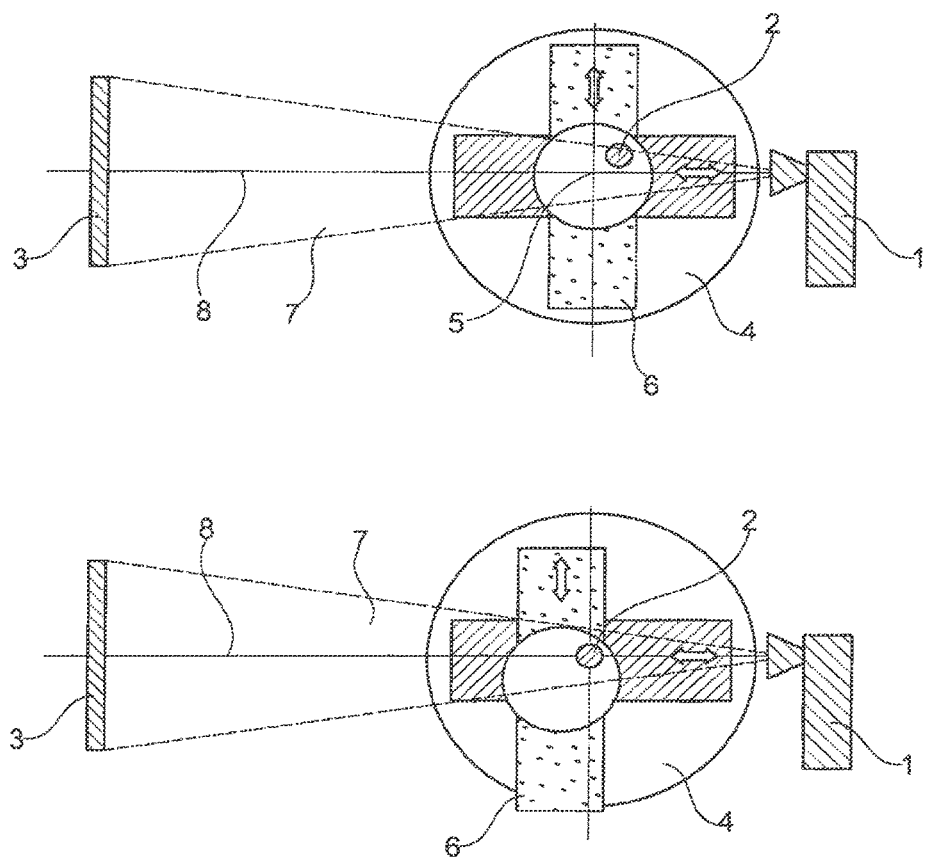
FIG. 1 is a schematic representation of a prior art method.

FIG. 1 shows a prior art procedure known from the state of the art. A test object 2 is arranged in an X-ray inspection system. The X-ray inspection system comprises an X-ray source 1 and a detector 3. Between these, a rotary table 4 is arranged, with an axis of rotation 5 running perpendicular to the plane of the page, which corresponds to the z-axis. On the rotary table 4 a positioning table 6 is attached, which enables a displacement of the test object which is arranged on it, in the plane of the page, the xy-plane. The x-axis is parallel to the surface of the detector 3 and in FIG. 1 runs vertically in the plane of the page. The result is that the y-axis runs horizontally in the plane of the page. The X-ray tube 1 emits a fan beam 7, the central beam 8 of which strikes detector 3 centrally. The central beam 8 corresponds to the y-axis.

The test object 2 is arranged non-centrally over the rotary table 4, i.e. outside its axis of rotation 5. In order to obtain the best possible image of the test object 2, the latter must, however, be arranged in the centre of the rotational movement. Thus the test object arranged on the positioning table 6 is displaced by means of the positioning table 6 in the x- and y-direction until it lies over the axis of rotation 5 of the rotary table 4 (see lower part of FIG. 1). The rotation of the test object 2 is now carried out by rotation of the rotary table 4 about its axis of rotation 5 and, in any rotation position of the test object 2, the central beam 8 passes through the latter. This described standard CT scanning method provides that the test object 2 is rotated in the fan beam 7 in order thus to obtain the individual projections which are converted into a tomogram by suitable software. During the rotation of the test object 2 it is decisive for the quality that the test object 2 is represented completely in every projection. Precisely in the range of very large enlargements it is very laborious to shift the area of interest into the rotation centre, i.e. over the axis of rotation 5 of the rotary table 4.

The solution approach described below is illustrated with reference to examples from DXR and CT, but can be used in the same way in the field of laminography. It represents a universal solution and can be used in many areas of an X-ray inspection installation.

Figure 2:
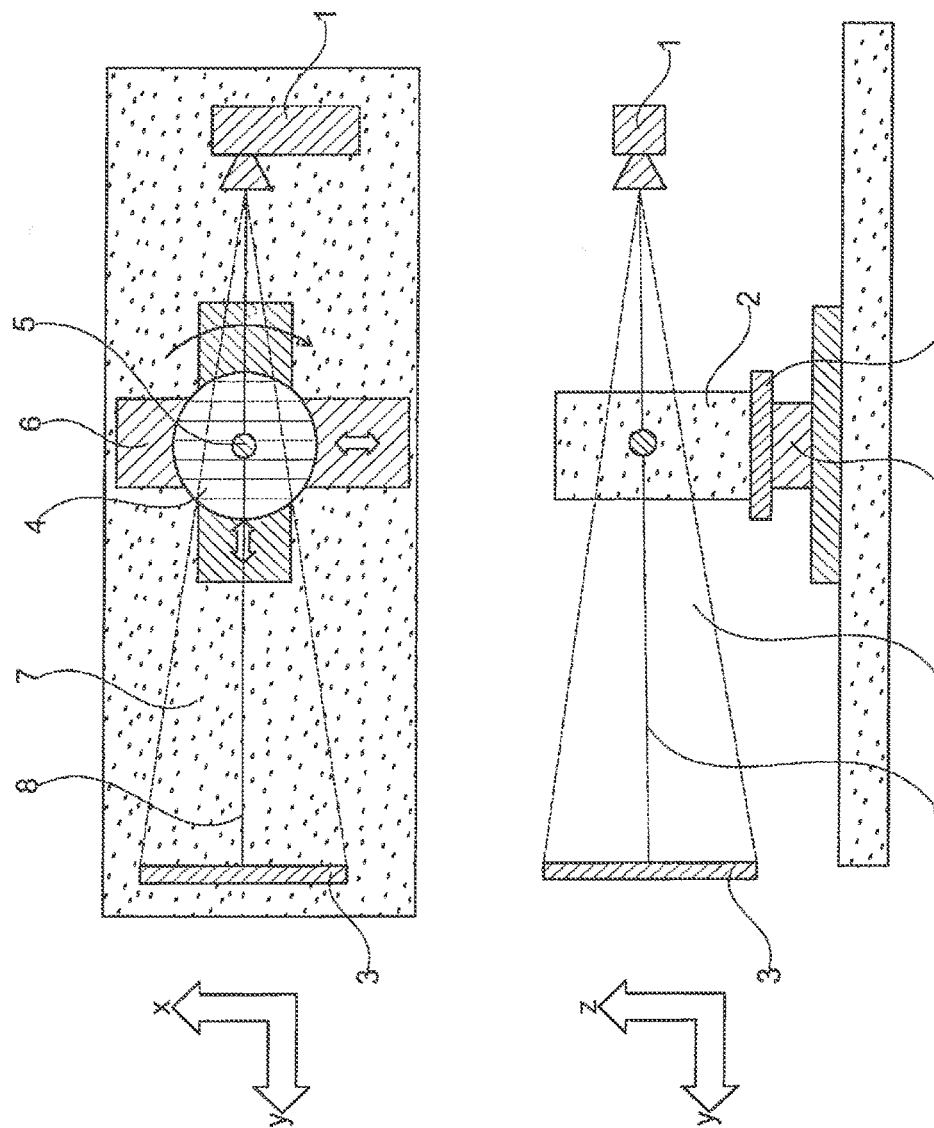
FIG. 2 is a simplified representation of an X-ray inspection system according to an embodiment of the invention.

FIG. 2 shows an X-ray inspection system according to an embodiment of the invention. It broadly corresponds to the X-ray inspection system described above with reference to FIG. 1. The difference is that the rotary table 4 is arranged on the positioning table 6 and not the other way round as described with reference to FIG. 1. In addition, the X-ray inspection system according to the invention also may include a lifting device 10 and a tilting axis 9 (see FIG. 5).

The solution approach according to the invention is to bring the axes into relationship with each other such that their common positioning represents the travel distance of a new-virtual-axis. For better understanding, the method is represented with reference to a "virtual axis of rotation" of a CT X-ray machine.

Assuming that the rotary table 4 is secured on a positioning table 6—with possibilities for linear movement in the xy-plane—it is now possible to proceed with the x-axis and the y-axis combined, with the result that the rotary table 4 moves on an orbit.

In order to realize a virtual axis of rotation, it is now necessary for the angle of rotation of the rotary table 4 to be positioned or moved in the defined relationship to the x- and y-axes. For this, the axis of rotation 5 is defined as master and the two axes x and y are positioned corresponding to the angle of rotation of the axis of rotation 5. The relationships for this are as follows according to the invention:

$$X = R \times \cos(\varphi - \varphi_0) + X_0$$

$$Y = R \times \sin(\varphi - \varphi_0) + Y_0$$

with

X: new target value of x-axis, $X_0$: starting value of the x-axis at the starting time of the virtual axis coupling, Y: new target value of y-axis, $Y_0$: starting value of the y-axis at the starting time of the virtual axis coupling, R: distance between the axis of rotation and the new virtual axis of rotation, $\varphi$: actual angle of the axis of rotation and $\varphi_0$: starting value of the axis of rotation at the starting time of the virtual axis coupling.

Figure 3:
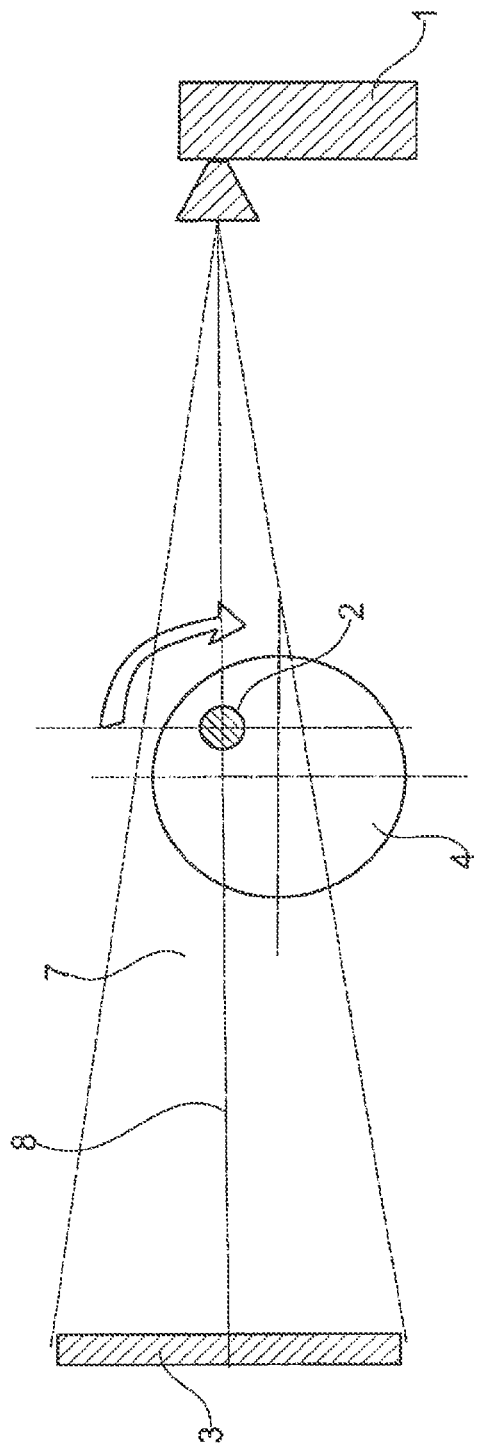
FIG. 3 is a schematic representation showing a virtual rotational axis.

This type of linking now makes it possible to rotate about any desired point in the x/y-plane, provided that the absolute travel distance limits of the x- and y-axis are not exceeded, as shown schematically in FIG. 3.

For further examination methods, the resultant new, virtual axis of rotation behaves as a real axis of rotation, i.e. the methods used in the X-ray examination such as, for example, a measuring range enlargement (DXR) or a CT-examination method (helical CT, etc.) can continue to be used without limitation.

Alternatively to the arrangements just described, instead of the rotary table 4, the imaging elements detector 3 and X-ray source 1 can also rotate about the test object 2 or be moved in the xy direction.

The conversion of the method of the virtual axis of rotation can, in modified form, be easily realized as a method of a viewing angle with any desired tilting point. An advantage is a fixed focus-object distance along the manipulation of the x-axis.

Figure 4:
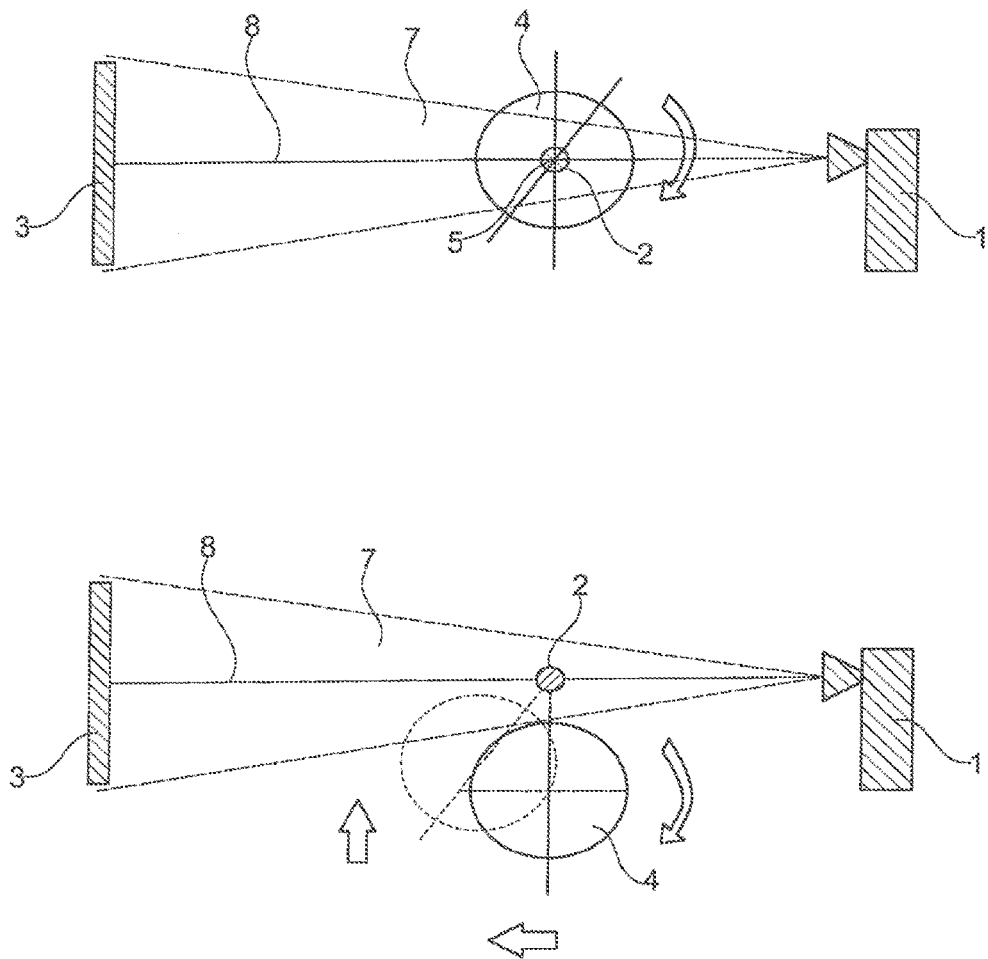
FIG. 4 is a schematic representation of a method with variable tilting angle.

FIG. 4 (representation in the xy-plane) shows, in the upper part, the standard case, i.e. the area around a point of interest in the test object 2 is examined at different viewing angles. For this, this point must be situated in the axis of rotation 5 of the rotary table 4. It is now possible, by means of the rotary table 4 to look at the point of interest at different viewing angles. It is important that the point of interest is situated in the axis of rotation 5 of the rotary table 4. Should this not be the case, the area around the point of interest would, in the case of significant enlargement, move out of the field of view of the detector 3.

The lower representation of FIG. 4 shows the possibility of tilting about any point on the x-axis. Through the superimposition of the axis of rotation 5 with the x- and y-axis there is the possibility of also examining the point of interest when the latter is not situated in the rotation centre of the rotary table 4. For this, use is made of the same method as described above. In the present representation, the point of interest is positioned in the central beam 8. From this position and the real axis position of the rotary table 4 it is possible to determine the value R (see above) and "activate" a virtual axis of rotation. It is thereby possible to examine the point of interest at any desired viewing angles. Thus, as soon as a new angle of rotation is set, the x- and y-axes respectively are automatically positioned according to the mathematical relationship described previously.

Due to an additional possibility of movement of the test object 2 in the z-direction (relative to the detector 3) in the case of a planar test object 2 tilting is thus possible at any desired point about an axis which is perpendicular to the xy-plane. This is explained with reference to FIG. 5.

Due to an additional tilting axis 9 of the rotary table 4 (alternatively this is also possible with a tilting movement of the detector-irradiation geometry) in conjunction with a lifting device 10 which moves the rotary table 4 along the z-axis, the possibility is created, in the case of a test object 2 at any desired point which is represented as area of interest 11, of tilting about an axis in any desired position. Assuming that a flat, rectangular sample is mounted as test object 2 on the centre of the rotary table 4, it is possible by the method described above, along the x-axis and in conjunction with a z-axis, to rotate any point of the sample about the z-axis. With the additional tilting axis 9, a further axis of rotation is formed, but now in the x direction, i.e. it is now additionally possible to also rotate any point about the x-axis. There is thus now the maximum degree of freedom to carry out the examination in an area of interest 11 about a point in the sample at all the viewing angles about x and z.

Any desired orientation of the coordinate system is in principle possible.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for rotating a test object in an X-ray inspection system, the X-ray inspection system comprising: an X-ray source having a central beam running in parallel to a y-axis; a detector; and a rotary table arranged between the X-ray source and the detector, the rotary table having a rotation axis defining a z-axis, being configured to be rotated about the z-axis, having a surface corresponding to an x-axis and the y-axis that is configured to secure a test object thereon, being arranged on a positioning table, which is configured to be moved parallel to an xy-plane between the X-ray source and the detector, the xy-plane being perpendicular to a surface of the detector extending parallel to the xz-plane, the method comprising:

securing the test object on the rotary table; and rotating the rotary table about the z-axis and simultaneously moving the positioning table in the xy-plane, wherein the angle of rotation φ of the rotary table has the following relationships to x- and y-positions of the positioning table:

$$X = R \times \cos(\varphi - \varphi_0) + X_0$$

$$Y = R \times \sin(\varphi - \varphi_0) + Y_0$$

with

X: a new target value of an x-axis, $X_0$: a starting value of the x-axis at a starting time of a virtual axis coupling, Y: a new target value of a y-axis, $Y_0$: a starting value of the y-axis at the starting time of the virtual axis coupling, R: a distance between an axis of rotation and a new virtual axis of rotation, φ: an actual angle of the axis of rotation, and $\varphi_0$: a starting value of the axis of rotation at the starting time of the virtual axis coupling.

2. A method for rotating a test object in an X-ray inspection system, the X-ray inspection system comprising: an X-ray source having a central beam running in parallel to a y-axis a detector; and a rotary table arranged between the X-ray source and the detector, the rotary table having a rotation axis defining a z-axis, being configured to be rotated about the z-axis, having a surface corresponding to an x-axis and the y-axis that is configured to secure a test object thereon, being arranged on a positioning table, which is configured to be moved parallel to an xy-plane between the X-ray source and the detector, the xy-plane being perpendicular to a surface of the detector extending parallel to the xz-plane, the method comprising:

securing the test object on the rotary table; and rotating the X-ray source in conjunction with the detector about the test object about a rotational axis parallel to the z-axis and simultaneously moving the X-ray source parallel to the xy-plane, wherein the angle of rotation φ of the rotary table has the following relationships to x- and y-positions of the positioning table:

$$X = R \times \cos(\varphi - \varphi_0) + X_0$$

$$Y = R \times \sin(\varphi - \varphi_0) + Y_0$$

with

X: a new target value of an x-axis, $X_0$: a starting value of the x-axis at a starting time of a virtual axis coupling, Y: a new target value of the y-axis, $Y_0$: a starting value of the y-axis at the starting time of the virtual axis coupling, R: a distance between an axis of rotation and a new virtual axis of rotation, φ: an actual angle of the axis of rotation, and $\varphi_0$: a starting value of the axis of rotation at the starting time of the virtual axis coupling.

3. The method according claim 1, wherein, before the described movements are carried out, the rotary table is moved along the z-axis and is tilted about a tilting axis running parallel to the x-axis, with the result that an area of interest lying within the test object lies at the same position in the coordinate system before and after the described tilting movement and translational movement.

4. The method according to claim 2, wherein, before the described movements are carried out, the rotary table is moved along the z-axis and is tilted about a tilting axis running parallel to the x-axis, with the result that an area of interest lying within the test object lies at the same position in the coordinate system before and after the described tilting movement and translational movement.

5. The method according to claim 1, further comprising moving the rotary table along the z-axis.

6. The method according to claim 1, further comprising tilting the rotary table about one or both of a tilting axis running parallel to the xy-plane and parallel to the x-axis.

7. The method according to claim 1, wherein the x-ray source, in conjunction with the detector, performs at least one of: rotating about the rotary table, moving parallel to the xy-plane with respect to the rotary table, moving parallel to the z-axis, and tilting about a tilting axis running parallel to the xy-plane.

8. The method according to claim 2, further comprising moving the rotary table along the z-axis.

9. The method according to claim 2, further comprising tilting the rotary table about one or both of a tilting axis running parallel to the xy-plane and parallel to the x-axis.

10. The method according to claim 2, wherein the x-ray source, in conjunction with the detector, performs at least one of: rotating about the rotary table, moving parallel to the xy-plane with respect to the rotary table, moving parallel to the z-axis, and tilting about a tilting axis running parallel to the xy-plane.

* * * * *